US009375258B2

(12) United States Patent
Kendrick

(10) Patent No.: US 9,375,258 B2
(45) Date of Patent: Jun. 28, 2016

(54) SURGICAL FORCEPS

(75) Inventor: Stephen M. Kendrick, Broomfield, CO (US)

(73) Assignee: Covidien LP, Mansfield, MA (US)

(*) Notice: Subject to any disclaimer, the term of this patent is extended or adjusted under 35 U.S.C. 154(b) by 1044 days.

(21) Appl. No.: 13/466,274

(22) Filed: May 8, 2012

(65) Prior Publication Data

US 2013/0304058 A1 Nov. 14, 2013

(51) Int. Cl.
A61B 18/14 (2006.01)
A61B 17/29 (2006.01)
A61B 17/285 (2006.01)
A61B 17/32 (2006.01)
A61B 18/12 (2006.01)
A61B 18/18 (2006.01)
A61B 18/00 (2006.01)

(52) U.S. Cl.
CPC ............ *A61B 18/1445* (2013.01); *A61B 17/29* (2013.01); *A61B 17/285* (2013.01); *A61B 17/320092* (2013.01); *A61B 18/1206* (2013.01); *A61B 18/1815* (2013.01); *A61B 2017/2946* (2013.01); *A61B 2018/00196* (2013.01); *A61B 2018/00916* (2013.01); *A61B 2018/1455* (2013.01); *A61B 2018/1807* (2013.01)

(58) Field of Classification Search
CPC ................. A61B 17/285; A61B 17/29; A61B 17/320092; A61B 18/1206; A61B 18/1445; A61B 18/1815; A61B 2017/2946; A61B 2018/00196; A61B 2018/00916; A61B 2018/1455; A61B 2018/1807; A61B 2018/4857
See application file for complete search history.

(56) References Cited

U.S. PATENT DOCUMENTS

| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| 5,344,424 A | 9/1994 | Roberts et al. |

(Continued)

FOREIGN PATENT DOCUMENTS

| CN | 201299462 | 9/2009 |
| DE | 2415263 A1 | 10/1975 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

Primary Examiner — Amanda Patton

(57) ABSTRACT

A forceps includes a housing defining a window and having an outer shaft extending therefrom. An end effector assembly disposed at a distal end of the outer shaft includes first and second jaw members including distal portions and proximal portions and movable between spaced-apart and approximated positions. An inner shaft is slidably disposed within the outer shaft such that, when the jaw members are disposed in the spaced-apart position, the inner shaft is disposed in a distal position. When the jaw members are moved to the approximated position, the proximal portions urge the inner shaft to a proximal position. An indicator member coupled to the inner shaft includes first and second indicators. The first indicator is visible through the window when the inner shaft is disposed in the distal position. The second indicator is visible through the window when the inner shaft is disposed in the proximal position.

5 Claims, 12 Drawing Sheets

(56) References Cited

U.S. PATENT DOCUMENTS

| | | | |
|---|---|---|---|
| D354,564 S | 1/1995 | Medema | |
| D358,887 S | 5/1995 | Feinberg | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| 6,775,575 B2 | 8/2004 | Bommannan et al. | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| 8,162,973 B2 | 4/2012 | Cunningham | |
| D661,394 S | 6/2012 | Romero et al. | |
| 2007/0043353 A1* | 2/2007 | Dycus | A61B 18/1445 606/51 |
| 2007/0260242 A1 | 11/2007 | Dycus et al. | |
| 2009/0182327 A1 | 7/2009 | Unger | |
| 2009/0261804 A1 | 10/2009 | McKenna et al. | |
| 2010/0057078 A1 | 3/2010 | Arts et al. | |
| 2011/0054469 A1 | 3/2011 | Kappus et al. | |
| 2011/0077648 A1 | 3/2011 | Lee et al. | |
| 2011/0196368 A1 | 8/2011 | Moses et al. | |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A3 | 9/2002 |
| WO | 2006/021269 A1 | 3/2006 |
| WO | 2005110264 A3 | 4/2006 |
| WO | 2008/040483 A1 | 4/2008 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

(56) References Cited

OTHER PUBLICATIONS

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.

Bergdahl et al. "Studies on Coagulation and the Development of an Automatic Computerized Bipolar Coagulator" J. Neurosurg, vol. 75, July 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report Ep 05004431.2 dated Jun. 2, 2005.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.

(56) References Cited

OTHER PUBLICATIONS

Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 11 006233.8 dated Feb. 2, 2012.
Int'l Search Report EP 11 007972.0 dated Dec. 28, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 153503.5 dated Mar. 5, 2012.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report EP 11 180183 dated Nov. 30, 2011.
Int'l Search Report EP 11 183265.5 dated Nov. 28, 2011.
Int'l Search Report EP 11 183476.8 dated Jan. 18, 2012.
Int'l Search Report EP 11 185028.5 dated Jan. 2, 2012.
Int'l Search Report EP 11 189521.5 dated Feb. 20, 2012.
Int'l Search Report EP 11 190723.4 dated Mar. 16, 2012.
Int'l Search Report EP 12 155726.8 dated May 25, 2012.
Int'l Search Report EP 12 155728.4 dated Jul. 4, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Int'l Search Report EP 10 185386.9 dated Jan. 10, 2011.
Int'l Search Report EP 10 185405.7 dated Jan. 5, 2011.
Int'l Search Report EP 11 168419.7 dated Oct. 20, 2011.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020528.9 dated Aug. 4, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 015215.8 dated Feb. 24, 2010.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report Ep 10 175559.3 dated May 25, 2012.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019.9 dated Aug. 22, 2011.
Int'l Search Report EP 10 182022.3 dated Mar. 11, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
U.S. Appl. No. 08/926,869, James G. Chandler.
U.S. Appl. No. 09/177,950, Randel A. Frazier.
U.S. Appl. No. 09/387,883, Dale F. Schmaltz.
U.S. Appl. No. 09/591,328, Thomas P. Ryan.
U.S. Appl. No. 12/336,970, Paul R. Sremeich.
U.S. Appl. No. 13/050,182, Glenn A. Horner.
U.S. Appl. No. 13/072,945, Patrick L. Dumbauld.
U.S. Appl. No. 13/080,383, David M. Garrison.
U.S. Appl. No. 13/085,144, Keir Hart.
U.S. Appl. No. 13/091,331, Jeffrey R. Townsend.
U.S. Appl. No. 13/102,573, John R. Twomey.
U.S. Appl. No. 13/102,604, Paul E. Ourada.
U.S. Appl. No. 13/108,093, Boris Chernov.

(56) References Cited

OTHER PUBLICATIONS

U.S. Appl. No. 13/108,129, Boris Chernov.
U.S. Appl. No. 13/108,152, Boris Chernov.
U.S. Appl. No. 13/108,177, Boris Chernov.
U.S. Appl. No. 13/108,196, Boris Chernov.
U.S. Appl. No. 13/108,441, Boris Chernov.
U.S. Appl. No. 13/108,468, Boris Chernov.
U.S. Appl. No. 13/111,642, John R. Twomey.
U.S. Appl. No. 13/111,678, Nikolay Kharin.
U.S. Appl. No. 13/113,231, David M. Garrison.
U.S. Appl. No. 13/157,047, John R. Twomey.
U.S. Appl. No. 13/162,814, Barbara R. Tyrrell.
U.S. Appl. No. 13/166,477, Daniel A. Joseph.
U.S. Appl. No. 13/166,497, Daniel A. Joseph.
U.S. Appl. No. 13/179,919, Russell D. Hempstead.
U.S. Appl. No. 13/179,960, Boris Chernov.
U.S. Appl. No. 13/179,975, Grant T. Sims.
U.S. Appl. No. 13/180,018, Chase Collings.
U.S. Appl. No. 13/183,856, John R. Twomey.
U.S. Appl. No. 13/185,593, James D. Allen, IV.
U.S. Appl. No. 13/204,841, Edward J. Chojin.
U.S. Appl. No. 13/205,999, Jeffrey R. Unger.
U.S. Appl. No. 13/212,297, Allan J. Evans.
U.S. Appl. No. 13/212,308, Allan J. Evans.
U.S. Appl. No. 13/212,329, Allan J. Evans.
U.S. Appl. No. 13/212,343, Duane E. Kerr.
U.S. Appl. No. 13/223,521, John R. Twomey.
U.S. Appl. No. 13/227,220, James D. Allen, IV.
U.S. Appl. No. 13/228,742, Duane E. Kerr.
U.S. Appl. No. 13/231,643, Keir Hart.
U.S. Appl. No. 13/234,357, James D. Allen, IV.
U.S. Appl. No. 13/236,168, James D. Allen, IV.
U.S. Appl. No. 13/236,271, Monte S. Fry.
U.S. Appl. No. 13/243,628, William Ross Whitney.
U.S. Appl. No. 13/247,778, John R. Twomey.
U.S. Appl. No. 13/247,795, John R. Twomey.
U.S. Appl. No. 13/248,976, James D. Allen, IV.
U.S. Appl. No. 13/249,013, Jeffrey R. Unger.
U.S. Appl. No. 13/249,024, John R. Twomey.
U.S. Appl. No. 13/251,380, Duane E. Kerr.
U.S. Appl. No. 13/277,373, Glenn A. Horner.
U.S. Appl. No. 13/277,926, David M. Garrison.
U.S. Appl. No. 13/277,962, David M. Garrison.
U.S. Appl. No. 13/293,754, Jeffrey M. Roy.
U.S. Appl. No. 13/306,523, David M. Garrison.
U.S. Appl. No. 13/306,553, Duane E. Kerr.
U.S. Appl. No. 13/308,104, John R. Twomey.
U.S. Appl. No. 13/312,172, Robert J. Behnke, II.
U.S. Appl. No. 13/324,863, William H. Nau, Jr.
U.S. Appl. No. 13/344,729, James D. Allen, IV.
U.S. Appl. No. 13/355,829, John R.Twomey.
U.S. Appl. No. 13/357,979, David M. Garrison.
U.S. Appl. No. 13/358,136, James D. Allen, IV.
U.S. Appl. No. 13/360,925, James H. Orszulak.
U.S. Appl. No. 13/400,290, Eric R. Larson.
U.S. Appl. No. 13/404,435, Kim V. Brandt.
U.S. Appl. No. 13/404,476, Kim V. Brandt.
U.S. Appl. No. 13/412,879, David M. Garrison.
U.S. Appl. No. 13/412,897, Joanna Ackley.
U.S. Appl. No. 13/421,373, John R. Twomey.
U.S. Appl. No. 13/430,325, William H. Nau, Jr.
U.S. Appl. No. 13/433,924, Keir Hart.
U.S. Appl. No. 13/448,577, David M. Garrison.
U.S. Appl. No. 13/460,455, Luke Waaler.
U.S. Appl. No. 13/461,335, James D. Allen, IV.
U.S. Appl. No. 13/461,378, James D. Allen, IV.
U.S. Appl. No. 13/461,397, James R. Unger.
U.S. Appl. No. 13/461,410, James R. Twomey.
U.S. Appl. No. 13/464,569, Duane E. Kerr.
U.S. Appl. No. 13/466,274, Stephen M. Kendrick.
U.S. Appl. No. 13/467,767, Duane E. Kerr.
U.S. Appl. No. 13/470,543, Sean T. Dycus.
U.S. Appl. No. 13/470,775, James D. Allen, IV.
U.S. Appl. No. 13/470,797, John J. Kappus.
U.S. Appl. No. 13/482,589, Eric R. Larson.
U.S. Appl. No. 13/483,733, Dennis W. Butcher.
U.S. Appl. No. 13/488,093, Kristin D. Johnson.
U.S. Appl. No. 13/491,853, Jessica E. Olson.
U.S. Appl. No. 13/537,517, David N. Heard.
U.S. Appl. No. 13/537,577, Tony Moua.
U.S. Appl. No. 13/550,322, John J. Kappus.
U.S. Appl. No. 13/571,055, Paul Guerra.
U.S. Appl. No. 13/571,821, Joseph D. Bucciaglia.
U.S. Appl. No. 13/584,194, Sean T. Dycus.

\* cited by examiner

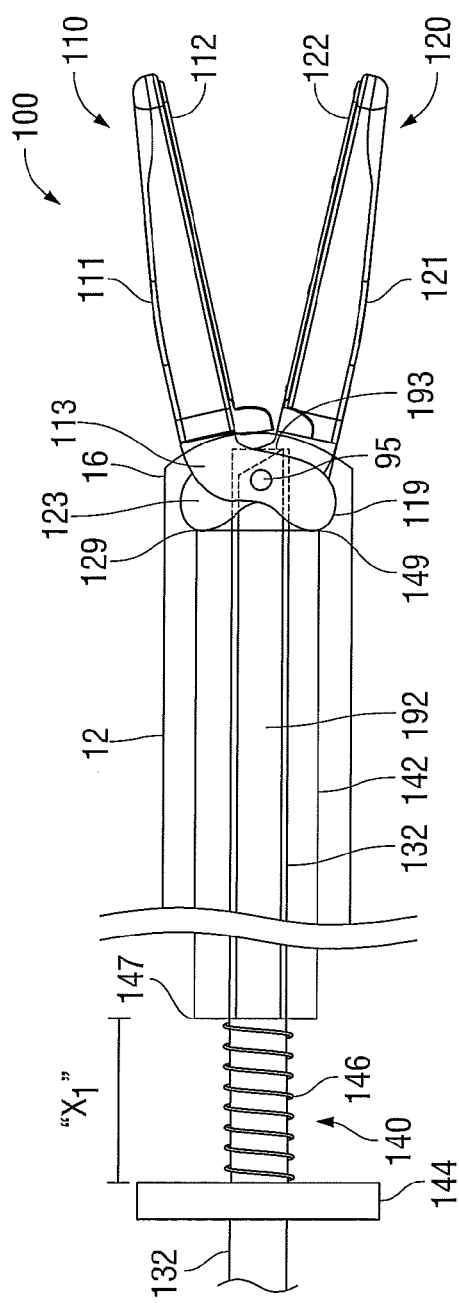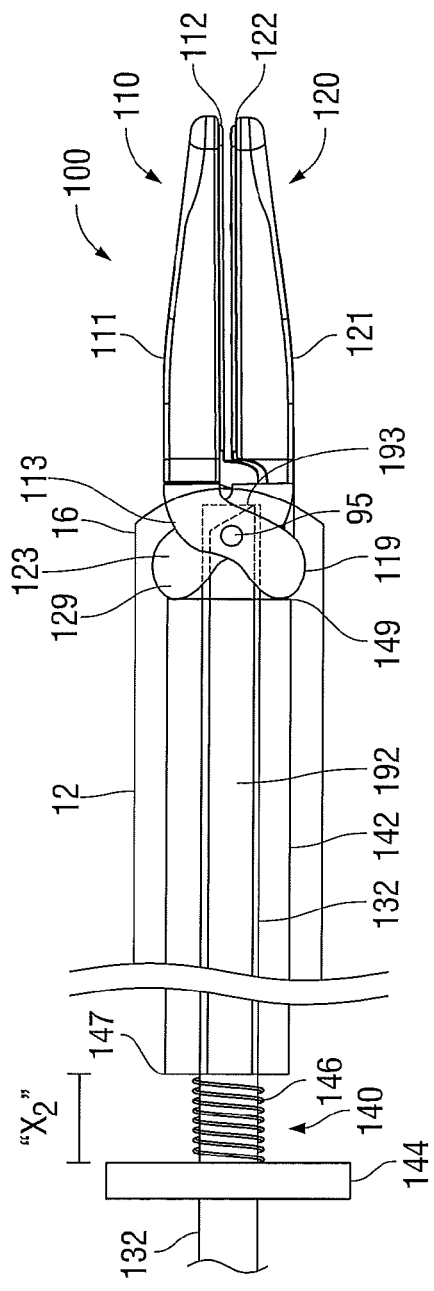
FIG. 5A
FIG. 5B

SURGICAL FORCEPS

BACKGROUND

1. Technical Field

The present disclosure relates to surgical instruments and, more particularly, to surgical forceps for grasping, treating, and/or dividing tissue.

2. Background of Related Art

A surgical forceps is a plier-like instrument which relies on mechanical action between its jaw members to grasp, clamp, and constrict tissue. Energy-based surgical forceps utilize both mechanical clamping action and energy, e.g., RF energy, ultrasonic energy, microwave energy, thermal energy, light energy, etc., to affect hemostasis by heating tissue and blood vessels to coagulate and/or cauterize tissue. Certain surgical procedures require more than simply coagulating/cauterizing tissue and rely on the unique combination of clamping pressure, precise energy control, and gap distance (i.e., the distance between opposing jaw members when closed about tissue) to "seal" tissue.

Typically, once tissue is treated, e.g., sealed, the surgeon has to accurately sever the tissue along the newly formed tissue seal. Accordingly, many surgical forceps have been designed which incorporate a knife or blade member that effectively severs the tissue after forming a tissue seal.

SUMMARY

As used herein, the term "distal" refers to that portion that is further from an operator while the term "proximal" refers to that portion that is closer to an operator. As used herein, the term "treat" refers to performing a surgical treatment to tissue using energy. The term "energy" refers broadly to include all types of energy used to treat tissue, e.g., RF energy, ultrasonic energy, microwave energy, thermal energy, light energy, etc. Further, any or all of the aspects described herein, to the extent they are consistent, may be used in conjunction with any of the other aspects described herein.

A forceps provided in accordance with aspects of the present disclosure includes a housing having an outer shaft extending distally therefrom. The housing defines a first indicator window therethrough. An end effector assembly is disposed at a distal end of the outer shaft. The end effector assembly includes first and second jaw members. One (or both) of the jaw members is movable relative to the other between a spaced-apart position and an approximated position for grasping tissue therebetween. Each jaw member includes a distal jaw portion defining a tissue-contacting surface and a proximal flange portion. An inner shaft is slidably disposed within the outer shaft and is operably positioned relative to the jaw members. As such, when the jaw members are disposed in the spaced-apart position, the inner shaft is disposed in a distal position. On the other hand, when the jaw members are moved to the approximated position, the proximal flanges of the jaw members urge the inner shaft proximally to a proximal position. A first indicator member is coupled to the inner shaft and includes first and second indicators. The first indicator is configured to be visible through the first indicator window of the housing when the inner shaft is disposed in the distal position. The second indicator is configured to be visible through the first indicator window of the housing when the inner shaft is disposed in the proximal position.

In one aspect, the forceps further includes a drive assembly including a drive bar operably coupled to the end effector assembly. The drive bar is sildably disposed within the outer shaft and is through and relative to the outer shaft between a first position and a second position for moving the jaw members between the spaced-apart position and the approximated position. Further, the inner shaft may be disposed about the drive bar.

In another aspect, a movable handle is provided. The movable handle is coupled to the drive assembly and extends from the housing. The movable handle movable between an initial position and a compressed position for translating the drive bar between the first position and the second position.

In another aspect, a second indicator member is coupled to the movable handle. In such aspects, a second indicator window is defined within the housing. The second indicator member includes first and second indicators configured such that the first indicator is visible through the second indicator window of the housing when the movable handle is disposed in the initial position and the second indicator is visible through the second indicator window of the housing when the movable handle is disposed in the compressed position.

In yet another aspect, a latch mechanism is provided for latching the movable handle in the compressed position.

Another forceps provided in accordance with aspects of the present disclosure includes a housing having an outer shaft extending distally therefrom and an end effector assembly disposed at a distal end of the outer shaft. The end effector assembly includes first and second jaw members. One (or both) of the jaw members is movable relative to the other between a spaced-apart position and an approximated position for grasping tissue therebetween. Each jaw member includes a distal jaw portion defining a tissue-contacting surface and a proximal flange portion. One (or both) of the tissue-contacting surfaces of the jaw members are configured to connect to a source of energy for transmitting energy between the tissue-contacting surfaces to treat tissue grasped therebetween. An inner shaft is slidably disposed within the outer shaft and is operably positioned relative to the jaw members such that, when the jaw members are disposed in the spaced-apart position, the inner shaft is disposed in a distal position and, when the jaw members are moved to the approximated position, the proximal flanges of the jaw members urge the inner shaft proximally to a proximal position. A first actuator is disposed within the housing. The first actuator is transitionable between an OFF position inhibiting the supply of energy to the tissue-contacting surface(s) and an ON position permitting the supply of energy to the tissue-contacting surface(s). The first actuator is biased towards the OFF position. A first actuation member is coupled to the inner shaft and is configured such that, when the inner shaft is disposed in the distal position, the first actuation member is spaced-apart from the first actuator such that the first actuator remains disposed in the OFF position and, when the inner shaft is moved to the proximal position, the first actuation member engages the first actuator to transition the first actuator to the ON position.

In one aspect, the forceps further includes a drive assembly including a drive bar operably coupled to the end effector assembly. The drive bar is sildably disposed within the outer shaft and is translatable between a first position and a second position for moving the jaw members between the spaced-apart position and the approximated position.

In another aspect, the forceps further includes a movable handle coupled to the drive assembly and extending from the housing. The movable handle is movable between an initial position and a compressed position for translating the drive bar between the first position and the second position.

A latch mechanism may also be provided for latching the movable handle in the compressed position.

In yet another aspect, the forceps further includes a second actuator disposed within the housing. The second actuator is transitionable between an OFF position inhibiting the supply of energy to the tissue-contacting surface(s) and an ON position permitting the supply of energy to the tissue-contacting surface(s). The second actuator is biased towards the OFF position. In such aspects, the forceps further includes a second actuation member coupled to the movable handle and configured such that, when the movable handle is disposed in the initial position, the second actuation member is spaced-apart from the second actuator such that the second actuator remains disposed in the OFF position and, when the movable handle is moved to the compressed position, the second actuation member engages the second actuator to transition the second actuator to the ON position.

In still another aspect, energy is inhibited from being supplied to the tissue-contacting surface(s) when one (or both) of the first and second actuators are disposed in the OFF position. Additionally or alternatively, a warning signal may be produced when the first actuator is disposed in the OFF position and the second actuator is disposed in the ON position and/or when the first actuator is disposed in the ON position and the second actuator is disposed in the OFF position.

In still yet another aspect, the forceps further includes an activation switch disposed on the housing. The activation switch is selectively activatable to supply energy to the tissue-contacting surface(s) for treating tissue grasped between the jaw members. In such aspects, the activation switch may be configured to be disabled when the first actuator (and/or the second actuator) is disposed in the OFF position.

Provided in accordance with aspects of the present disclosure is another forceps that includes an end effector assembly having first and second jaw members. One (or both) of the jaw members is movable relative to the other between a spaced-apart position and an approximated position for grasping tissue therebetween. Each jaw member includes a distal jaw portion defining a tissue-contacting surface and a proximal flange portion. An inner shaft is operably positioned relative to the jaw members and is configured such that, when the jaw members are disposed in the spaced-apart position, the inner shaft is disposed in a distal position and, when the jaw members are moved to the approximated position, the proximal flanges of the jaw members urge the inner shaft proximally to a proximal position. A knife assembly including a knife is movable between a retracted position and an extended position. In the extended position, the knife extends between the jaw members to cut tissue grasped therebetween. A trigger assembly including a trigger coupled to the knife assembly is also provided. The trigger is movable between an un-actuated position and an actuated position for moving the knife between the retracted position and the extended position, respectively. The trigger assembly and inner shaft are operably positioned relative to one another such that, when the inner shaft is disposed in the distal position, the inner shaft interferes with the trigger to inhibit movement of the trigger to the actuated position and, when the inner shaft is disposed in the proximal position, the trigger is permitted to move to the actuated position.

In one aspect, the forceps further includes a housing having an outer shaft extending distally therefrom. The end effector assembly is disposed at a distal end of the outer shaft. The inner shaft is slidably disposed within the outer shaft.

In another aspect, the forceps further includes a drive assembly having a drive bar operably coupled to the end effector assembly. The drive bar is sildably disposed within the outer shaft and is translatable between a first position and a second position for moving the jaw members between the spaced-apart position and the approximated position.

In still another aspect, the forceps further includes a movable handle coupled to the drive assembly and extending from the housing. The movable handle is movable between an initial position and a compressed position for translating the drive bar between the first position and the second position.

In yet another embodiment, the trigger assembly is disposed within the housing, while the trigger extends from the housing.

BRIEF DESCRIPTION OF THE DRAWINGS

Various aspects of the present disclosure are described herein with reference to the drawings wherein like reference numerals identify similar or identical elements:

FIG. 5A is a longitudinal, cross-sectional view of the distal end of the forceps of FIG. 1 including the inner shaft assembly, wherein the jaw members are disposed in the spaced-apart position;

FIG. 5B is a longitudinal, cross-sectional view of the distal end of the forceps of FIG. 1 including the inner shaft assembly, wherein the jaw members are disposed in the approximated position;

DETAILED DESCRIPTION

The operating features and inter-cooperating components of a surgical instrument provided in accordance with the present disclosure are shown in the Figures and described hereinbelow. More specifically, the surgical instrument is shown as a forceps 10, although the present disclosure is equally applicable for use with any other suitable surgical instrument. Obviously, different connections and considerations apply to each particular type of instrument; however, the novel aspects of the present disclosure remain generally consistent regardless of the particular type of instrument used. For the purposes herein, forceps 10 is generally described.

Figure 1:
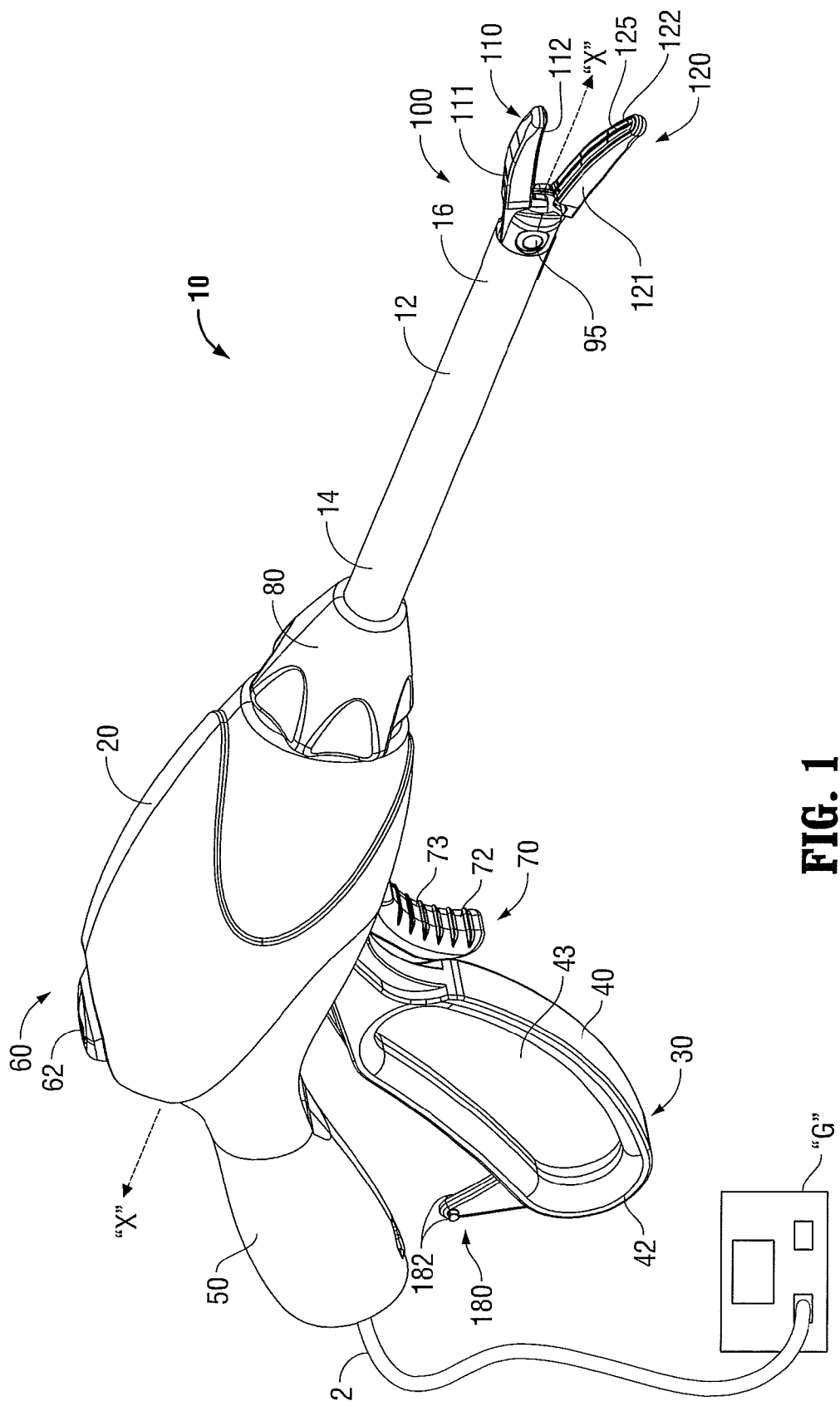
FIG. 1 is a side, perspective view of a forceps provided in accordance with the present disclosure.

Referring to FIG. 1, forceps 10 is configured for use in various surgical procedures and includes a housing 20, a handle assembly 30, a switch assembly 60, a trigger assembly 70, a rotating assembly 80, and an end effector assembly 100 that mutually cooperate to grasp, treat, and divide tissue. Forceps 10 further includes an outer shaft 12 having a distal end 16 configured to mechanically engage end effector assembly 100 and a proximal end 14 configured to mechanically engages housing 20. A cable 2 connects forceps 10 to an energy source, e.g., a generator "G," such that, upon activation of activation switch 62 of switch assembly 60, energy is supplied to end effector assembly 100 to treat tissue grasped therein, as will be described in greater detail below. Alternatively, forceps 10 may be configured as a battery-powered instrument having a portable battery (not shown) and generator (not shown) disposed within housing 20.

Handle assembly 30 includes a fixed handle 50 and a movable handle 40. Fixed handle 50 is integrally associated with housing 20 and movable handle 40 is movable relative to fixed handle 50 between an initial position and a compressed position (or multiple compressed positions), as will be explained in greater detail below, to impart movement of jaw members 110, 120 of end effector assembly 100 between a spaced-apart position (FIG. 2A) and an approximated position (FIG. 2B) (or multiple approximated positions) to grasp tissue therebetween. Rotating assembly 80 is operatively associated with housing 20 and is rotatable about a longitudinal axis "X-X" to rotate end effector assembly 100 about longitudinal axis "X-X." Trigger assembly 70, as will be described in greater detail below, is selectively actuatable to deploy a knife 192 (FIG. 3) from outer shaft 12 to between jaw members 110, 120 to cut tissue grasped therebetween.

Figure 2A:
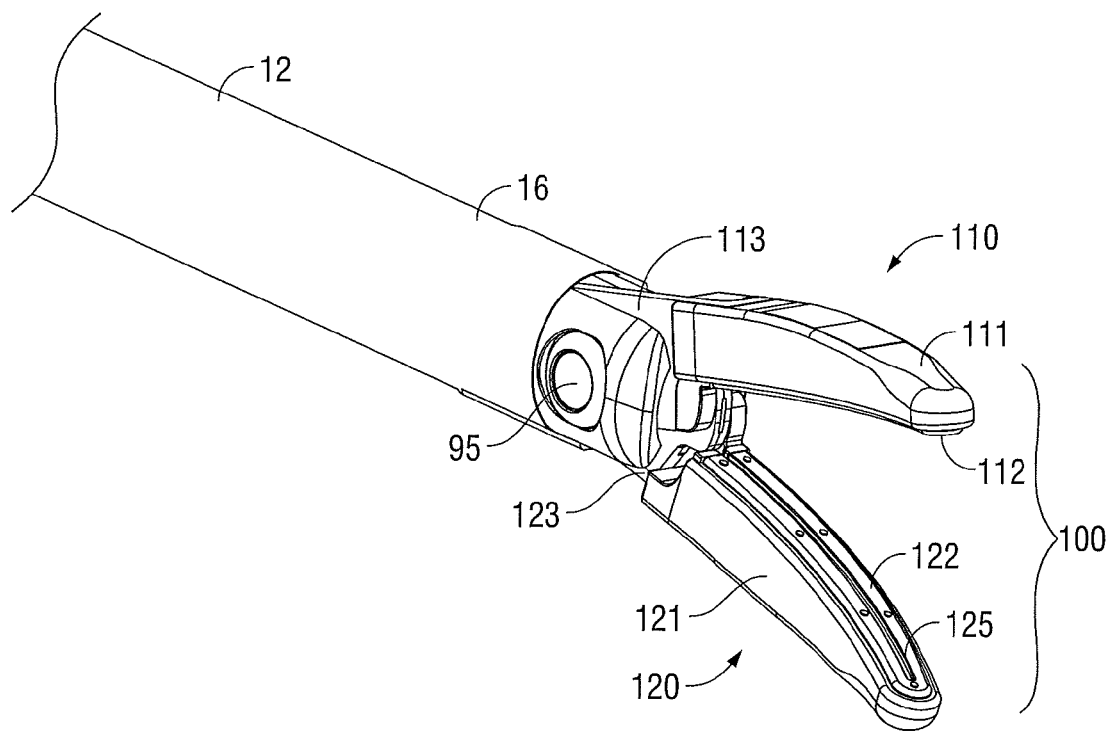
FIG. 2A is a side, perspective view of the distal end of the forceps of FIG. 1 wherein jaw members of the end effector assembly of the forceps are disposed in a spaced-apart position.
Figure 2B:
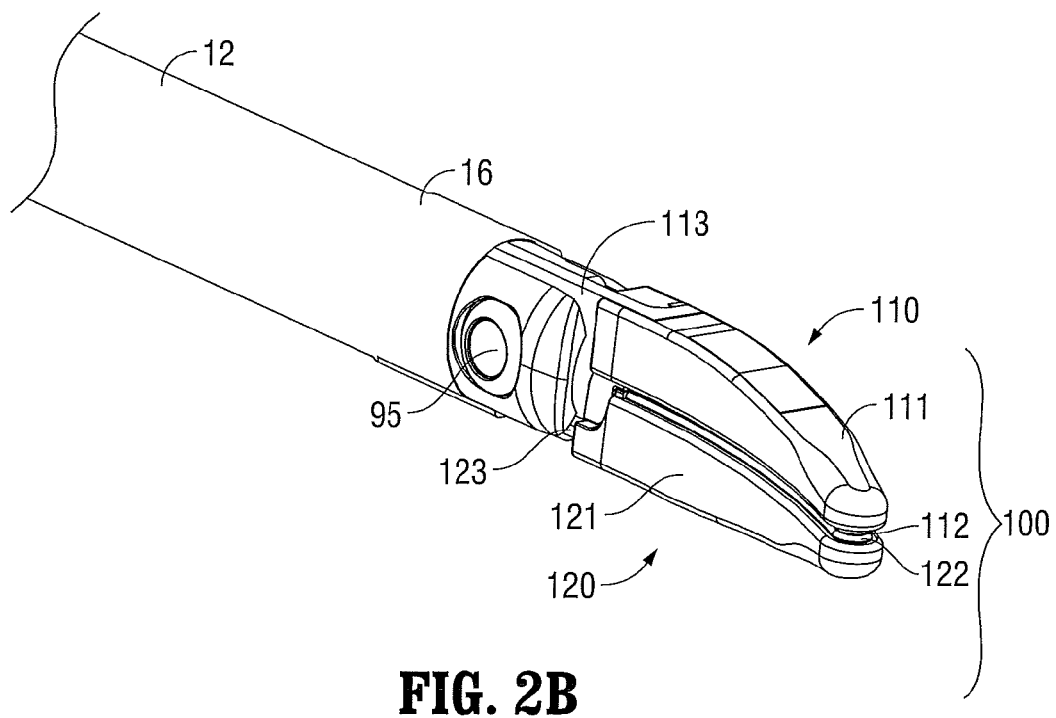
FIG. 2B is a side, perspective view of the distal end of the forceps of FIG. 1 wherein the jaw members are disposed in an approximated position.
Figure 3:
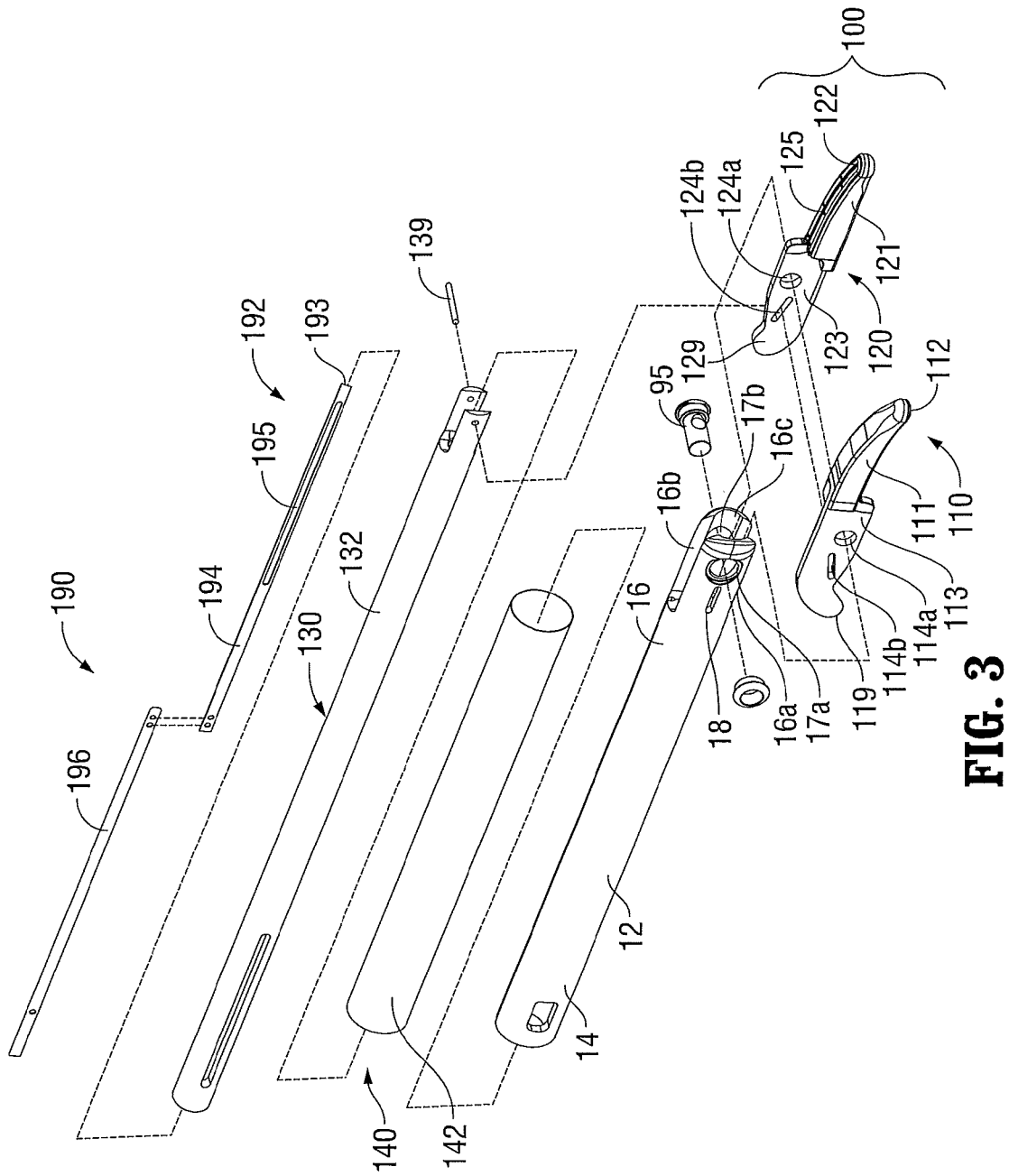
FIG. 3 is a side, perspective view of the distal end of the forceps of FIG. 1 shown with parts separated.

With additional reference to FIGS. 2A-2B and 3, end effector assembly 100 is attached at distal end 16 of outer shaft 12 and includes a pair of opposing jaw members 110, 120. End effector assembly 100 is designed as a bilateral assembly, i.e., both jaw members 110 and 120 are movable relative to one another and outer shaft 12 about a pivot pin 95, although end effector assembly 100 may alternatively be configured as a unilateral end effector assembly. Further, jaw members 110, 120 of end effector assembly 100 are curved to facilitate manipulation of tissue and to provide better "line of sight" for accessing targeted tissues, although other configurations may also be provided.

Continuing with reference to FIGS. 1-3, each jaw member 110, 120 includes a distal jaw portion 111, 121 that defines a tissue-contacting surface 112, 122, respectively, thereon, and a proximal flange 113, 123 extending distally from the respective distal jaw portion 111, 121 thereof for operably mounting jaw members 110, 120, respectively, at distal end 16 of outer shaft 12. Either or both tissue-contacting surfaces 112, 122 are adapted to connect to the source of energy, e.g., generator "G," for conducting energy therebetween and through tissue grasped between jaw members 110, 120 to treat, e.g., seal, tissue. More specifically, wire(s) (not shown) may extend from electrosurgical cable 2 (FIG. 1), through housing 20 and shaft 12, ultimately connecting to one or both of tissue-contacting surfaces 112, 122, although other configurations are also contemplated. The tissue-contacting surfaces 112, 122 and distal jaw portions 111, 121 of one or both of jaw members 110, 120, respectively, may cooperate to define a longitudinally-oriented knife channel 125 that is configured to permit reciprocation of knife 192 therethrough.

Proximal flanges 113, 123, as will be described in greater detail below, each include a proximally-extending knob 119, 129, respectively, that is configured to translate inner shaft 142 of inner shaft assembly 140 between a distal position (FIG. 4A) and a proximal position (FIG. 4B) upon movement of jaw members 110, 120 between the spaced-apart and approximated positions. Proximal flanges 113, 123 of jaw members 110, 120, respectively, each further include a pivot aperture 114a, 124a, respectively, defined therethrough, and an angled cam slot 114b, 124b, respectively, defined therethrough. Distal end 16 of outer shaft 12 includes a bifurcated portion including first and second flanges 16a and 16b, respectively, that define a channel 16c therebetween for receiving jaw members 110 and 120. Each flange 16a, 16b defines a pivot aperture 17a, 17b, respectively, therethrough for receipt of pivot pin 95, and a longitudinal cam slot 18.

During assembly, pivot pin 95 is inserted through pivot aperture 17a of flange 16a of outer shaft 12, pivot aperture 124a of proximal flange 123 of jaw member 120, pivot aperture 114a of proximal flange 113 of jaw member 110, and pivot aperture 17b of flange 16b of shaft 12 to pivotably engage jaw members 110, 120 at distal end 16 of outer shaft 12. Angled cam slots 114b, 124b of jaw members 110, 120 and longitudinal cam slots 18 of flanges 16a, 16b of outer shaft 12 are configured to operably couple jaw members 110, 120 to drive assembly 130. More specifically, drive pin 139, which is engaged to drive sleeve 132 at the distal end thereof, is configured to be slidably received within cam slots 114b, 124b of jaw members 110, 120, respectively, and cam slots 18 of flanges 16a, 16b of outer shaft 12 such that proximal translation of drive sleeve 132, e.g., upon pivoting of movable handle 40 from the initial position to the compressed position, drive pin 139 is translated proximally relative to and through slots 114b, 124b, and 18 to pivot jaw members 110, 120 from the spaced-apart position (FIG. 2A) to the approximated position (FIG. 2B) to grasp tissue therebetween. Distal translation of drive sleeve 132, on the other hand, urges drive pin 139 distally though slots 18, 114b, 124b to urge jaw members 110, 120 from the approximated position (FIG. 2B) back to the spaced-apart position (FIG. 2A).

Figure 4A:
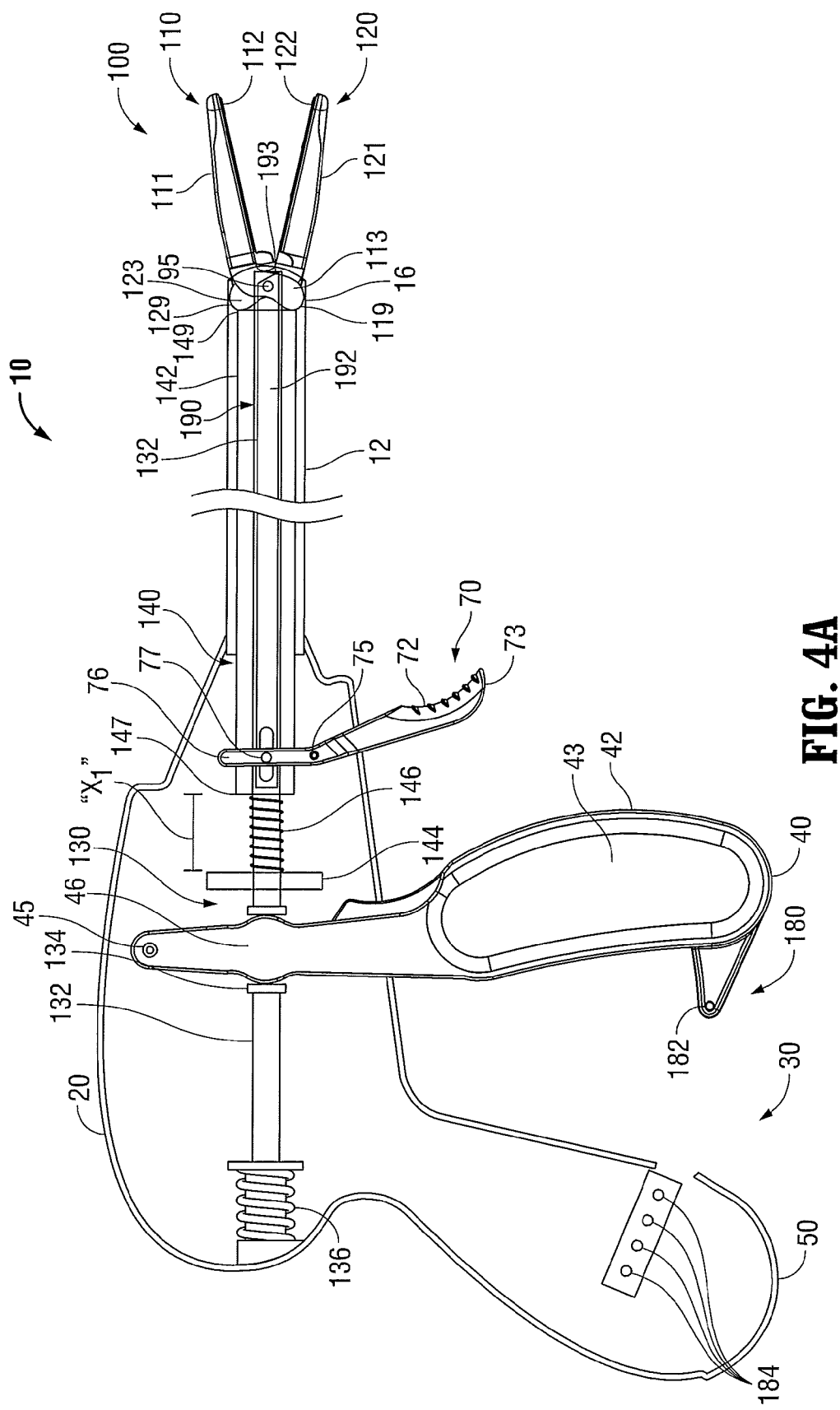
FIG. 4A is a longitudinal, cross-sectional view of the forceps of FIG. 1 wherein the jaw members are disposed in the spaced-apart position.
Figure 4B:
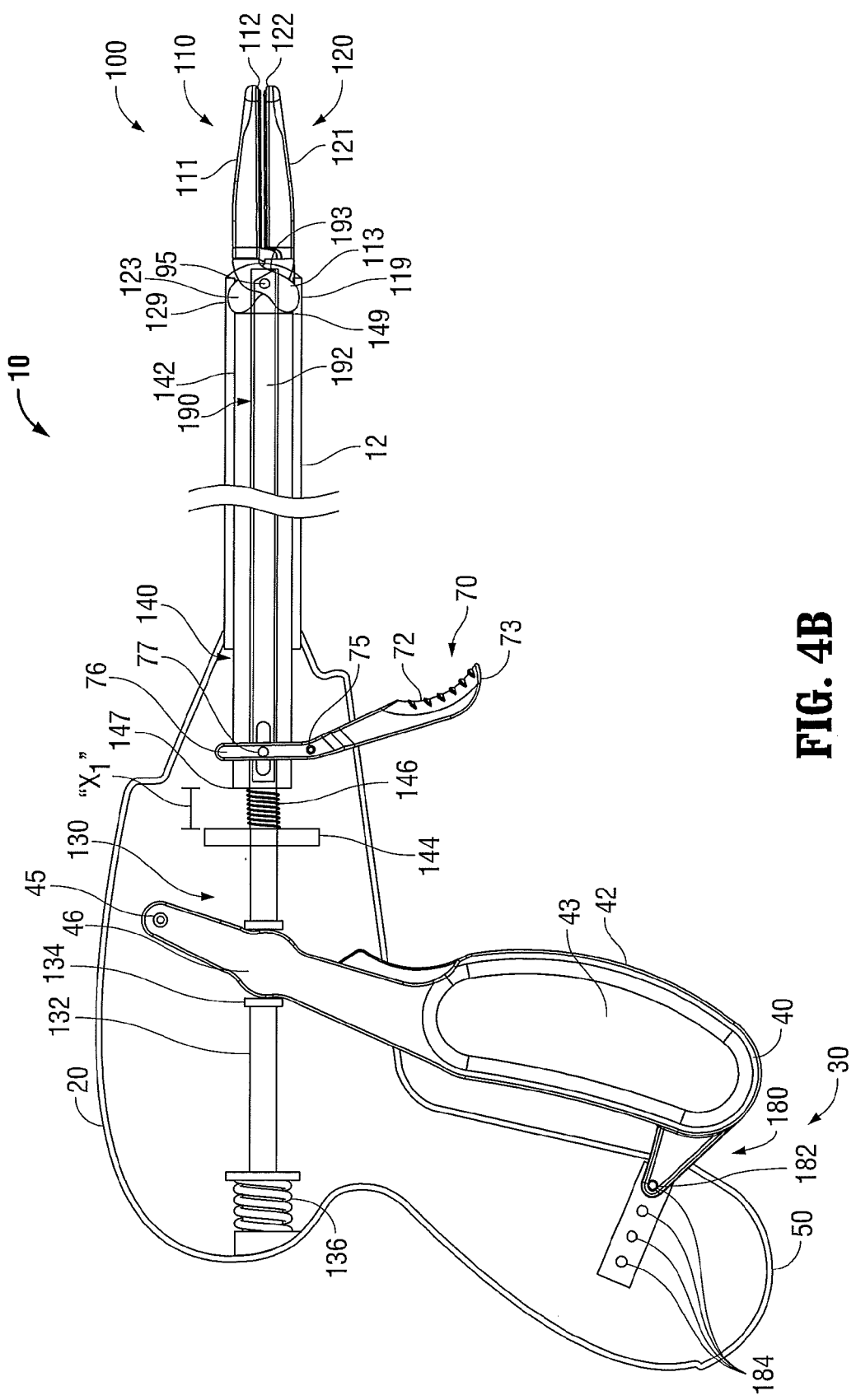
FIG. 4B is a longitudinal, cross-sectional view of the forceps of FIG. 1 wherein the jaw members are disposed in the approximated position.

Turning now to FIGS. 4A-4B, in conjunction with FIGS. 1-3, movable handle 40 includes a lever 42 defining a finger hole 43 and a bifurcated arm 46 extending upwardly from lever 42 and into housing 20. Arm 46 is bifurcated to define first and second spaced-apart flanges that are pivotably coupled to housing 20 at the free ends thereof via pivot pin 45. The flanges of arm 46 extend on either side of drive assembly 130 and are coupled thereto to facilitate movement of jaw members 110, 120 between the spaced-apart position and the approximated position. More specifically, arm 46 extends upwardly on either side of and is engaged to mandrel 134. Mandrel 134, in turn, is fixedly engaged about drive sleeve 132. Due to this configuration, upon pivoting of movable handle 40 about pivot pin 45 and relative to fixed handle 50 from the initial position (FIG. 4A) to the compressed position (FIG. 4B), mandrel 134 and, thus, drive sleeve 132 are translated proximally, thereby translating drive pin 139 proximally through angled cam slots 114b, 124b of jaw members 110, 120, respectively and cam slots 18 of flanges 16a, 16b of outer shaft 12 to pivot jaw members 110, 120 from the spaced-apart position (FIGS. 2A and 4A) to approximated position (FIGS. 2B and 4B). On the other hand, return of movable handle 40 towards the initial position returns drive sleeve 132 distally, thereby returning jaw members 110, 120 towards the spaced-apart position. A spring 136 may also be provided to bias mandrel 134 distally, thereby biasing movable handle 40 towards the initial position and jaw members 110, 120 towards the spaced-apart position.

Movable handle 40 may further include a latch assembly 180 extending proximally therefrom. Latch assembly 180 is configured such that, upon movement of movable handle 40 from the initial position to the compressed position, pegs 182 of latch assembly 180 are engaged within corresponding notches 184 defined within fixed handle 40 of housing 20 for latching movable handle 40 in the compressed position and, thus, jaw members 110, 120 in the approximated position grasping tissue therebetween. Latch assembly 180 may include a plurality of spaced-apart notches 184, as shown in FIGS. 4A-4B, for latching movable handle 40 at various different compressed positions corresponding to various different approximated positions of jaw members 110, 120, each defining a different gap distance between tissue-contacting surfaces 112, 122 of jaw members 110, 120, respectively. Other suitable latching mechanisms may also be provided.

With reference to FIGS. 1-4B, forceps 10 may further incorporate a knife assembly 190 for cutting tissue grasped between jaw members 110, 120. Knife assembly 190 includes a knife 192 that is configured for reciprocation through outer shaft 12 and knife channels 125 of jaw members 110, 120 between a retracted position, wherein knife 192 is positioned proximally of distal jaw portions 111, 121 of jaw members 110, 120, respectively, and an extended position, wherein knife 192 extends at least partially through knife channels 125 of jaw members 110, 120 to cut tissue grasped therebetween. Knife 192 includes a distal blade 193 configured to facilitate cutting tissue upon translation of knife 192 between jaw members 110, 120, and a elongated body portion 194. Body portion 194 of knife 190 defines a longitudinal slot 195 extending therethrough that is configured to receive pivot pin 95 and drive pin 139 to permit translation of knife 192 about pivot pin 95 and drive pin 139. Knife 192 is engaged to knife drive rod 196 at the proximal end thereof. Knife drive rod 196, in turn, As will be described in greater detail below, knife drive rod 196 is selectively translatable, e.g., upon actuation of trigger 72 assembly 70, through outer shaft 12 and relative to end effector assembly 100 to translate knife 192 between the retracted and extended position.

With continued reference to FIGS. 1-4B, trigger assembly 70 includes a trigger 72 having a toggle member 73 and a bifurcated arm 76 extending upwardly from toggle member 73 and into housing 20. Trigger 72 is pivotably coupled to housing 20 via pivot pin 75, which extends through an intermediate portion of trigger 72. Arm 76 is bifurcated to define first and second spaced-apart flanges to permit passage of arm 76 about drive sleeve 132 of drive assembly 130. An engagement pin 77 extends between the flanges of arm 76 of trigger 72 and through slots defined within both inner sleeve 142 and drive sleeve 132 to engage knife drive rod 196. Accordingly, upon pivoting of trigger 72 about pivot pin 75 and relative to housing 20 from an un-actuated position to an actuated position, knife drive rod 196 is pushed distally to thereby translate knife 192 from the retracted position to the extended position to cut tissue grasped between jaw members 110, 120. On the other hand, return of trigger 72 to the un-actuated position pulls knife drive rod 196 proximally to thereby translate knife 192 back to the retracted position. A spring (not shown) may be provided for biasing trigger 72 towards the un-actuated position, thereby biasing knife 192 towards the retracted position.

Turning now to FIGS. 4A-4B and 5A-5B, forceps 10 incorporates an inner shaft assembly 140 generally including an inner shaft 142, a base member 144, and a spring 146 configured to bias inner shaft 142 distally. As will be described in greater detail below, inner shaft 142 is movable between a distal (biased) position and a proximal position (or multiple proximal positions) upon movement of jaw members 110, 120 from the spaced-apart position to the approximated position(s). More specifically, inner shaft 142 is independent of and slidably disposed within outer shaft 12, while also being independent of and sildably disposed about drive sleeve 132, which is disposed about knife drive rod 196. Spring 146 is interdisposed between proximal end 147 of inner shaft 142 and base member 144 to bias distal end 149 of inner shaft 142 distally into abutment with knobs 119, 129 of proximal flanges 113, 123 of jaw members 110, 120, respectively. Thus, due to the configuration of knobs 119, 129, which extend proximally from proximal flanges 113, 123 of jaw members 110, 120, respectively, inner shaft 142 is biased by spring 146 to the distal position when jaw members 110, 120 are disposed in the spaced-apart position (FIG. 4A), but is urged proximally by knobs 119, 129 to the proximal position when jaw members 110, 120 are disposed in the approximated position (FIG. 4B). In the spaced-apart position of jaw members 110, 120 and, thus, the distal position of inner shaft 142, proximal end 147 of inner shaft 142 is spaced a distance "$X_1$" from base member 144. In the approximated position of jaw members 110, 120, on the other hand, corresponding to the proximal position of inner shaft 142, proximal end 147 of inner shaft is spaced a relatively smaller distance "$X_2$" from base member 144.

As will become more apparent in view of the various embodiments of the present disclosure described in detail in turn below, translation of inner shaft 142 between the distal and proximal positions upon movement of jaw members 110, 120 between the spaced-apart position and approximated positions indicates to the user the relative position of jaw members 110, 120 and/or operates a control mechanism to control deployment of knife 192 and/or the supply of energy to tissue-contacting surfaces 112, 122 depending on the relative position of jaw members 110, 120. For purposes of understanding and illustration, the embodiments below are discussed separately; however, the features of any or all of the embodiments disclosed herein may be used in conjunction with the features of any or all of the other embodiments disclosed herein.

Figure 6:
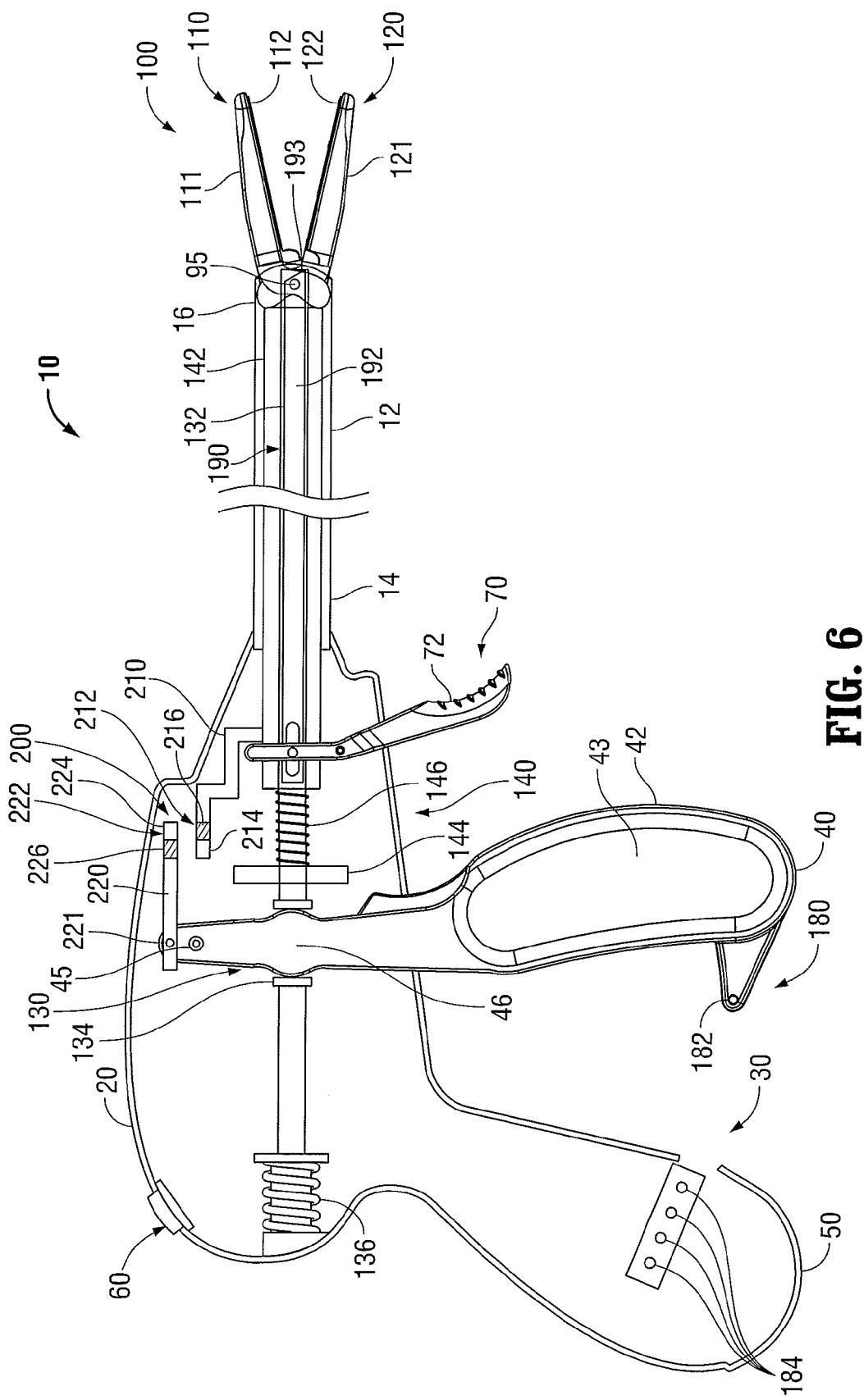
FIG. 6 is a longitudinal, cross-sectional view of another forceps provided in accordance with the present disclosure.
Figure 7A:
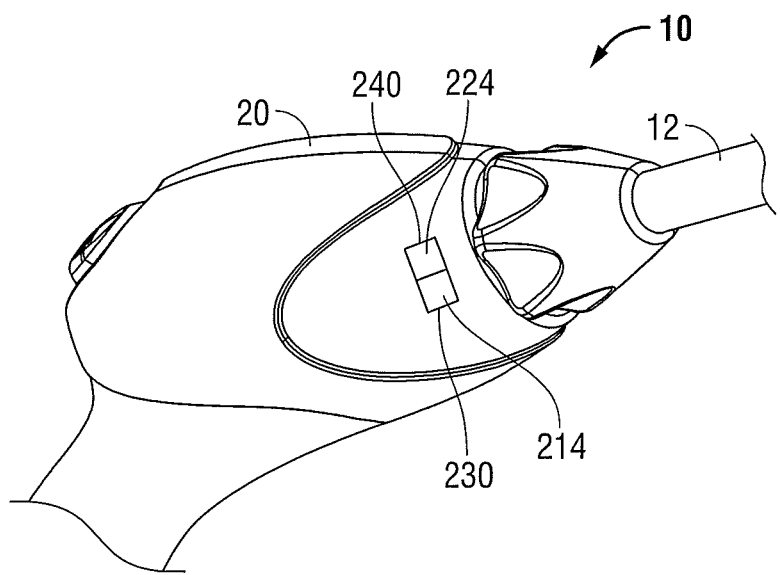
FIG. 7A is a side, perspective view of a portion of the housing of the forceps of FIG. 6 with the first and second indicator windows indicating that the jaw members are disposed in the spaced-apart position and the handle assembly is disposed in an initial position, respectively.
Figure 7B:
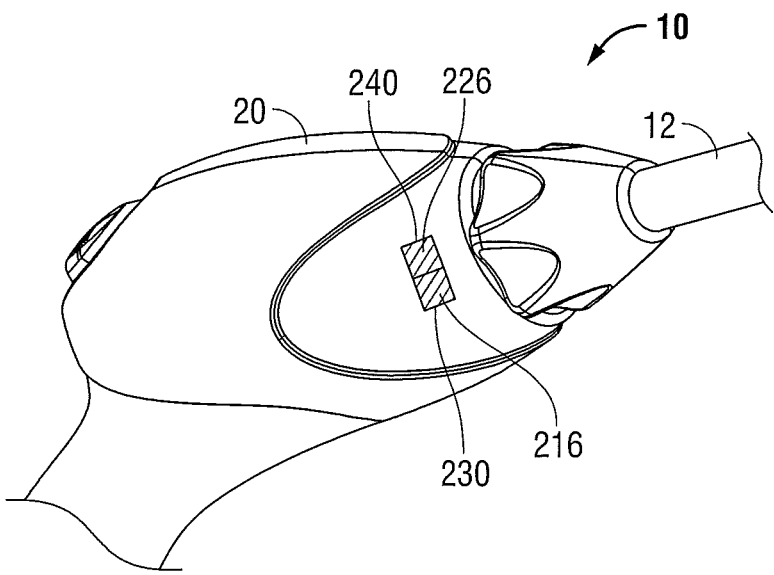
FIG. 7B is a side, perspective view of a portion of the housing of the forceps of FIG. 6 with first and second indicator windows indicating that the jaw members are disposed in the approximated position and the handle assembly is disposed in a compressed position, respectively.

Turning now to FIGS. 6-7B, forceps 10 is shown including an indicator mechanism 200. Indicator mechanism 200 generally includes a first indicator member 210 coupled to inner shaft 142, a second indicator member 220 coupled to movable handle 40, and a pair of indicator windows 230, 240 defined within housing 20. First indicator member 210 is engaged to and extends proximally from inner shaft 142 such that movement of inner shaft 142 between the distal and proximal positions effects corresponding movement of first indicator member 210 between first and second positions. First indicator member 210 further includes an indicating section 212 defining a first indicator 214 and a second indicator 216. Indicating section 212 is disposed adjacent indicator window 230 of housing 20 such that, upon movement of jaw members 110, 120 between the spaced-apart and approximated positions to move inner shaft 142 between the distal and proximal positions and, thus, first indicator member 210 between the first position, wherein first indicator 214 is positioned adjacent to and visible through first indicator window 230, and the second position, wherein second indicator 216 is positioned adjacent to and visible through first indicator window 230. Such a feature allows the user to quickly ascertain the relative position of jaw members 110, 120 in instances where jaw members 110, 120 themselves are not readily visible. When jaw members 110, 120 are disposed in an intermediate position, e.g., between the spaced-apart and approximated positions, a portion of each of first and second indicators 214, 216, respectively, would be visible through first indicator window 230, indicating to the user that jaw members 110, 120 are disposed in an intermediate position. This may indicate to the user the thickness of tissue grasped between jaw members 110, 120 or alert the user to potential problems. One or more intermediate indicators (not explicitly shown) disposed between first and second indicators 214, 216, respectively, may also be provided to more specifically indicate the relative spacing between jaw members 110, 120, e.g., for embodiments where jaw members 110, 120 are movable to multiple approximated positions.

Indicating section 212 may alternatively be disposed on inner shaft 142 (or first indicator member 210 may be disposed in any other suitable position) and first indicator window 230 may be positioned accordingly such that first indicator 214 is visible through first indicator window 230 when jaw members 110, 120 are disposed in the spaced-apart position and second indicator 216 is visible through first indicator window 230 when jaw members 110, 120 are disposed in the approximated position.

With continued reference to FIGS. 6-7B, second indicator member 220 is pivotably coupled to the free end of bifurcated arm 46 of movable handle 40 via pivot pin 221 and extends distally therefrom. Pivot pin 221 is disposed above pivot pin 45 of movable handle 40 such that pivoting of lever 42 of movable handle 40 from the initial position to the compressed position to pull drive sleeve 132 proximally and move jaw members 110, 120 from the spaced-apart position to the approximated position effects distal translation of second indicator member 220 from a first position to a second position. When movable handle 40 is moved to the compressed position (or one of the multiple compressed positions), pegs 182 of latch assembly 180 are engaged within one of the sets of notches 184 defined within fixed handle 50 to latch movable handle 40 in that compressed position and, thus, jaw members 110, 120 in the corresponding approximated position. That is, second indicator member 220 is moved from the first position to the second position upon latching of latch assembly 180.

Second indicator member 220 further includes an indicating section 222 defining a first indicator 224 and a second indicator 226. Indicating section 222 is disposed adjacent second indicator window 240 of housing 20 such that, upon movement of movable handle 40 from the initial position to the compressed position to latch movable handle 40, second indicator member 220 is moved from the first position, wherein first indicator 224 is positioned adjacent to and visible through second indicator window 240, to the second position, wherein second indicator 226 is positioned adjacent to and visible through second indicator window 240. Such a feature allows the user to quickly ascertain the relative position of movable handle 40, e.g., whether movable handle 40 is disposed in the initial position, the compressed position, or a position therebetween (wherein a portion of each of first and second indicators 224, 226, respectively, are visible through second indicator window 240), and/or whether latch assembly 180 is engaged to latch jaw members 110, 120 in the approximated position (or one of the approximated positions). Similarly as described above with respect to first indicator member 210, second indicator member 220 may likewise include one or more intermediate indicators (not explicitly shown) disposed between first and second indicators 224, 226, respectively, e.g., for embodiments where jaw members 110, 120 are movable to multiple approximated positions.

Each of the first and second indicators 214, 224 and 216, 226 of the first and second indicator members 210, 220, respectively, may include different colors, patterns, letters, numerals, symbols, indicia, etc. configured such that a user can quickly and easily ascertain which indicator 214, 216 is visible through first indicator window 230 and which indicator 224, 226 is visible through second indicator window 240. In use, when jaw members 110, 120 are disposed in the spaced-apart position, first indicators 214, 224 are visible through windows 230, 240, respectively. On the other hand, when jaw members 110, 120 are latched in the approximated position, second indicators 216, 226 are visible through windows 230, 240. Likewise, at positions between the spaced-apart and approximated positions (or where multiple approximated positions are provided), portions of both indicators 214, 216 and 224, 226 (or one or more intermediate indicators) are visible through windows 230, 240, respectively. In instances where there is a deviation from the above configuration, the user is alerted to a potential problem, e.g., that jaw members 110, 120 are not properly approximated and/or that movable handle 40 is not properly latched in the compressed position.

Figure 8:
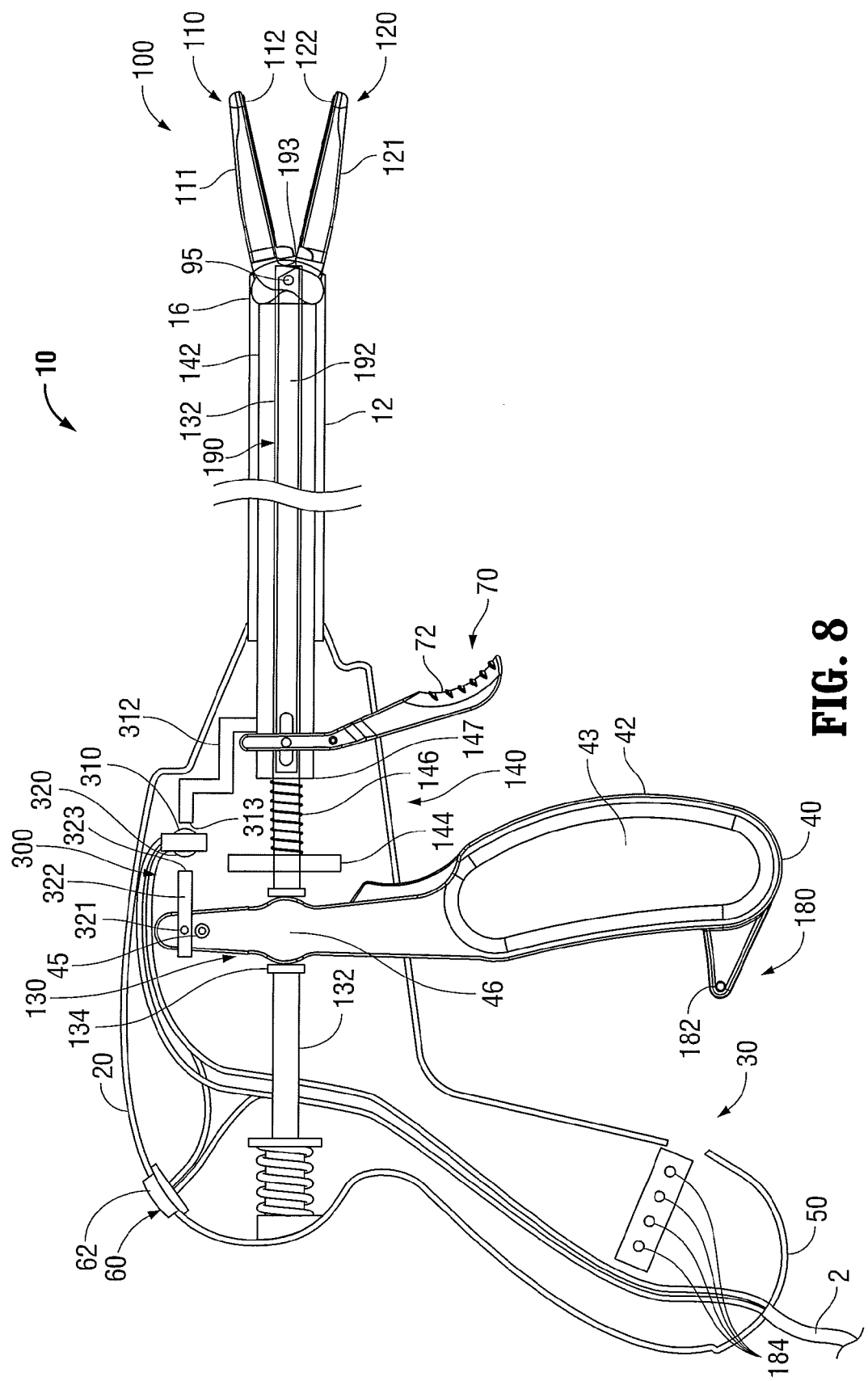
FIG. 8 is a longitudinal, cross-sectional view of another forceps provided in accordance with the present disclosure.

Turning now to FIG. 8, forceps 10 is shown including a control mechanism 300. Control mechanism 300 includes a first actuator 310 operably positioned relative to inner shaft 142 and a second actuator 320 operably positioned relative to movable handle 40. First actuator 310 is electrically coupled to activation switch 62 of switch assembly 60 and/or generator "G" (FIG. 1), and is selectively actuatable under the urging of first actuation member 312, which is engaged to and extends proximally from inner shaft 142. First actuator 310 may include a tactile actuator movable between an OFF position and an ON position, an incremental tactile actuator movable between an OFF position and a plurality of incremental ON positions, or any other suitable actuator, sensor, or switch mechanism. First actuator 310 is positioned such that, upon movement of jaw members 110, 120 from the spaced-apart position to the approximated position, inner shaft 142 is translated to the proximal position thereby translating first actuation member 312 proximally such that proximal end 313 of first actuation member 312 is urged into contact with first actuator 310 to actuate first actuator 310 from the OFF position to (one of) the ON position(s). Alternatively, first actuator 310 may be positioned to be actuated via proximal end 147 of inner shaft 142 upon movement of inner shaft 142 to the proximal position, obviating the need for actuation member 312.

Second actuator 320, as mentioned above, is operably positioned relative to movable handle 40. Similar to first actuator 310, second actuator 320 may include a tactile actuator, an incremental tactile actuator, or any other suitable actuator, sensor, or switch mechanism. A second actuation member 322 is pivotably coupled to the free end of bifurcated arm 46 of movable handle 40 via pivot pin 321 and extends distally therefrom. Pivot pin 321 is disposed above pivot pin 45 of movable handle 40 such that pivoting of lever 42 of movable handle 40 from the initial position to the compressed position to move jaw members 110, 120 from the spaced-apart position to the approximated position and latch jaw members 110, 120 in the approximated position effects distal translation of second actuation member 322 such that distal end 323 of second actuation member 322 is urged into contact with second actuator 320 to actuate second actuator 320 from the OFF position to (one of) the ON position(s).

As mentioned above, first and second actuators 310, 320 of control mechanism 300 may be coupled to activation switch 62 of switch assembly 60 and/or the generator "G." More specifically, first and second actuators 310, 320 may be configured to signal switch assembly 60 to enable activation switch 62 only when first and second actuators 310, 320 are disposed in the ON position. In such a configuration, the user is only permitted to selectively apply energy to tissue-contacting surfaces 112, 122 of jaw members 110, 120, respectively, when both first and second actuators 310, 320 are disposed in the ON position, thus indicating that jaw members 110, 120 are properly disposed in the approximated position and that movable handle 40 is latched in the compressed position. In other words, when one or both of first and second actuators 310, 320 are disposed in the OFF position, activation switch 62 is disabled. Alternatively or additionally, first and second actuators 310, 320 may be coupled to the generator "G" (FIG. 1) to signal generator "G" (FIG. 1) to permit the supply of energy from generator "G" (FIG. 1) to tissue-contacting surfaces 112, 122 only when first and second actuators 310, 320 are disposed in the ON position. First and second actuators 310, 320 may further be configured to signal the generator "G" (FIG. 1) to display and/or otherwise indicate to the user when jaw members 110, 120 are not properly disposed in the approximated position e.g., when first actuator 310 is in the OFF position, and/or when movable handle 40 is not properly latched in the compressed position, e.g., when second actuator 320 is in the OFF position.

In configurations where one or both of actuators 310, 320 are configured as incremental actuators, the generator "G" (FIG. 1) may process the signals received from actuators 310, 320 to determine whether the positions of movable handle 40 and jaw members 110, 120 are consistent with one another, e.g., whether the positioning of jaw members 110, 120 as indicated by inner shaft assembly 140 is consistent with the corresponding position of movable handle 40. If the signals are consistent, normal operation may be permitted, e.g., energy may be supplied from generator "G" (FIG. 1) to tissue-contacting surfaces 112, 122 of jaw members 110, 120, respectively. On the other hand, if the signals are not consistent, an error may be displayed by generator "G" (FIG. 1) or may otherwise be indicated, e.g., audibly. The generator "G" (FIG. 1) may further be configured to employ specific control parameters for controlling the supply of energy to tissue-contacting surfaces 112, 122 of jaw members 110, 120, respectively, depending on the signal received from either or both of actuators 310, 320 which, in turn, are dependent upon the relative position of jaw members 110, 120 and movable handle 40, respectively. For example, the desired control parameters for energy delivery when jaw members 110, 120 are spaced further-apart, e.g., grasping thicker tissue therebetween, may be different from those when jaw members 110, 120 are closer-together, e.g., grasping less thick tissue therebetween.

Figure 9:
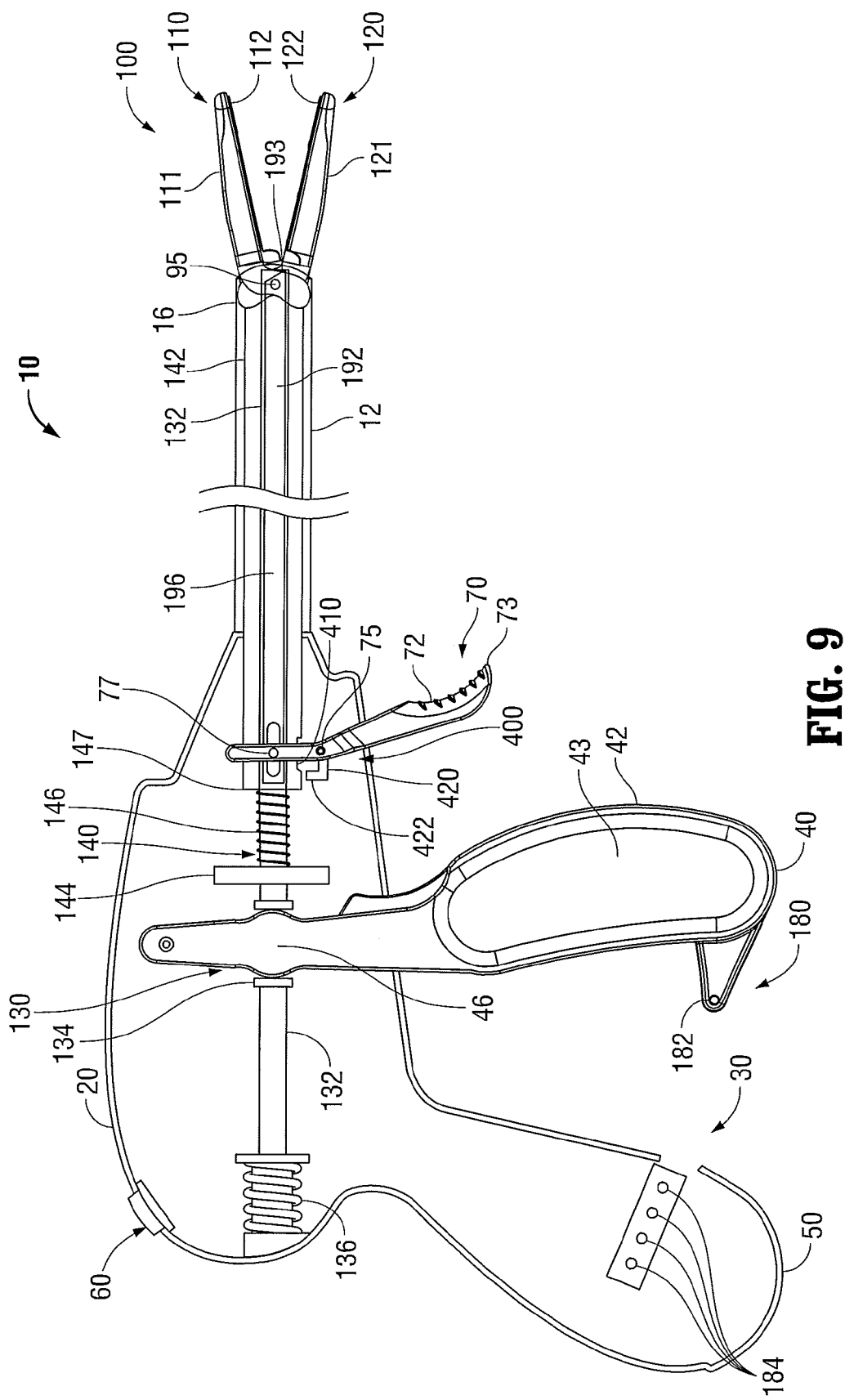
FIG. 9 is a longitudinal, cross-sectional view of another forceps provided in accordance with the present disclosure.
Figure 10A:
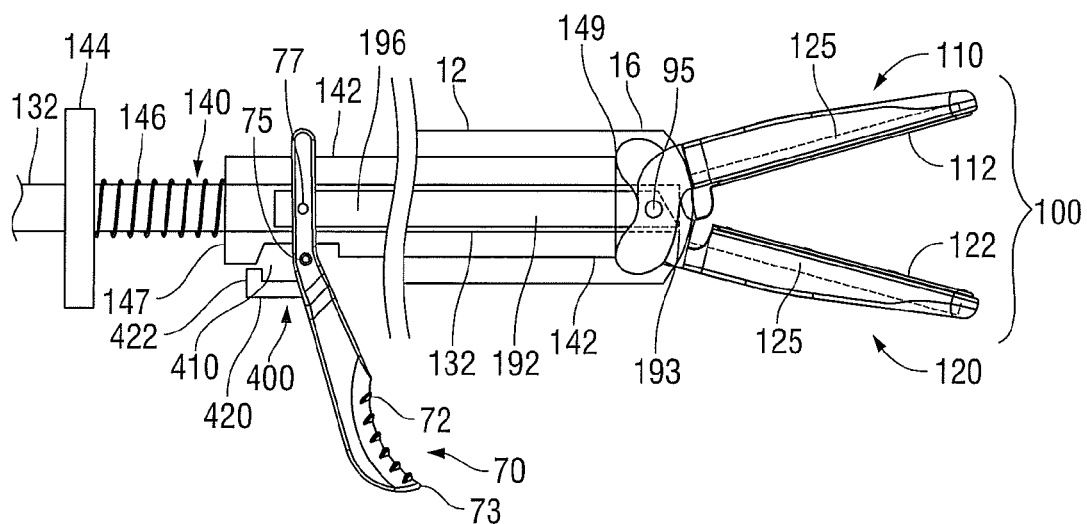
FIG. 10A is a longitudinal, cross-sectional view of the distal end of the forceps of FIG. 9 including the inner shaft assembly and the trigger assembly, wherein the jaw members are disposed in a spaced-apart position, the trigger is disposed in an un-actuated position, and the knife is disposed in a retracted position.
Figure 10B:
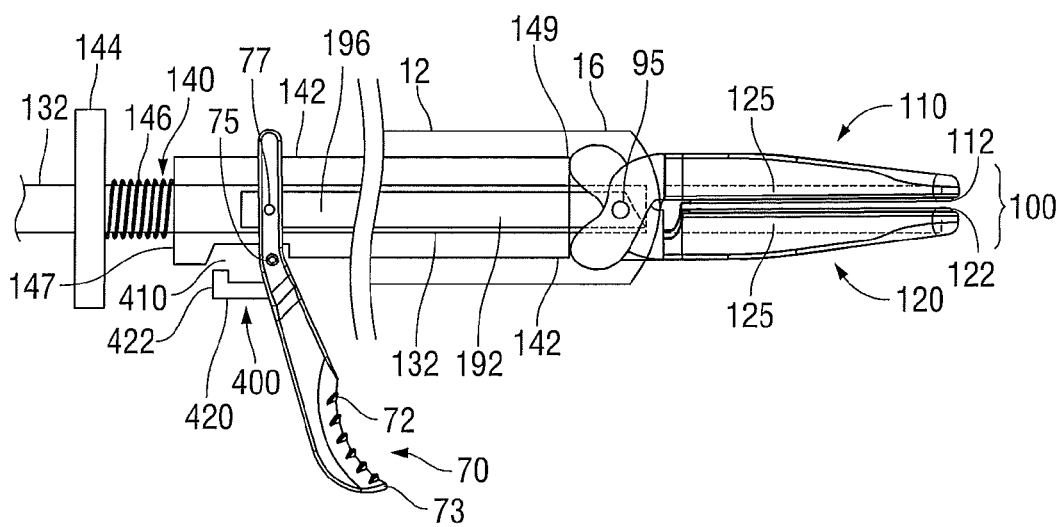
FIG. 10B is a longitudinal, cross-sectional view of the distal end of the forceps of FIG. 9 including the inner shaft assembly and the trigger assembly, wherein the jaw members are disposed in an approximated position, the trigger is disposed in an un-actuated position, and the knife is disposed in the retracted position.
Figure 10C:
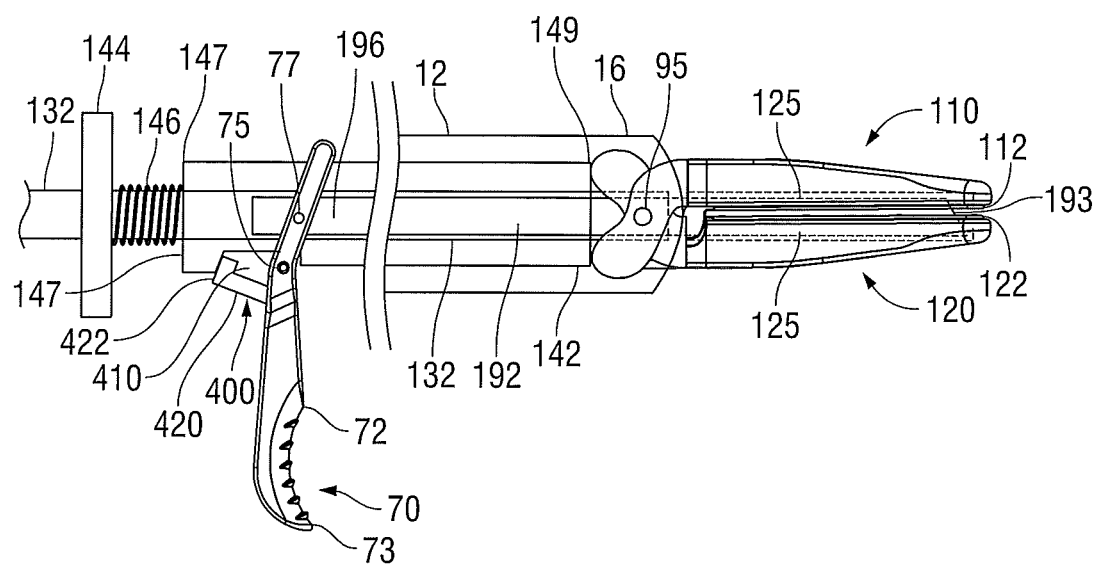
FIG. 10C is a longitudinal, cross-sectional view of the distal end of the forceps of FIG. 9 including the inner shaft assembly and the trigger assembly, wherein the jaw members are disposed in the approximated position, the trigger is disposed in an actuated position, and the knife is disposed in an extended position.

Turning now to FIGS. 9-10C, forceps 10 is shown incorporating a knife safety mechanism 400 configured to inhibit actuation of trigger 72 of trigger assembly 70 when jaw members 110, 120 are disposed in the spaced-apart position, thereby inhibiting deployment of knife 192 to the extended position when jaw members 110, 120 are disposed in the spaced-apart position. Knife safety mechanism 400 includes a cutout 410 defined within inner shaft 142 and a safety lockout arm 420 engaged to and extending from trigger 72.

As best shown in FIG. 10A, when jaw members 110, 120 are disposed in the spaced-apart position and, correspondingly, inner shaft 142 is disposed in the distal position, interference member 422, which is disposed at the free end of safety lockout arm 420, is positioned adjacent the outer surface of inner shaft 142 to inhibit knife 192 from being deployed. More specifically, in order to deploy knife 192 between jaw members 110, 120 to cut tissue therebetween, trigger 72 is rotated about pivot pin 75 from the un-actuated position to the actuated position to translate engagement pin 77 distally, thereby translating knife drive rod 196 distally and, thus, knife 192 distally to the extended position. However, with inner shaft 142 disposed in the distal position, rotation of trigger 72 from the actuated position to the un-actuated position is inhibited due to the abutment of interference member 422 with the outer surface of inner shaft 142. Accordingly, deployment of knife 192 is inhibited.

Referring now to FIGS. 10B-10C, as jaw members 110, 120 are moved to the approximated position, inner shaft 142, as described above, is urged from the distal position to the proximal position, wherein cut-out 410 defined within inner shaft 142 is aligned with interference member 422 of safety lockout arm 420 of trigger 72. With cut-out 410 and interference member 422 aligned with one another, trigger 72 is permitted to be rotated from the un-actuated position (FIG. 10B) to the actuated position (FIG. 10C) to advance knife 192 distally between jaw members 110, 120 to the extended position to cut tissue grasped therebetween with distal blade 193 of knife 192. More specifically, the alignment of cut-out 410 and interference member 422 allows interference member 422 to be received within cut-out 410 (rather than abutting the outer surface of inner shaft 142), thus permitting trigger 72 to be pivoted to the actuated position.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
   an end effector assembly including first and second jaw members, at least one of the jaw members movable relative to the other between a spaced-apart position and an approximated position for grasping tissue therebetween, each jaw member including a distal jaw portion defining a tissue-contacting surface and a proximal flange portion;

an inner shaft operably positioned relative to the jaw members, wherein, when the jaw members are disposed in the spaced-apart position, the inner shaft is disposed in a distal position, and wherein, when the jaw members are moved to the approximated position, the proximal flanges of the jaw members urge the inner shaft proximally to a proximal position;

a knife assembly including a knife movable between a retracted position and an extended position, wherein the knife extends between the jaw members to cut tissue grasped therebetween;

a trigger assembly including a trigger coupled to the knife assembly, the trigger movable between an un-actuated position and an actuated position for moving the knife between the retracted position and the extended position, respectively; and a lockout arm engaged to the trigger and extending therefrom, wherein, when the inner shaft is disposed in the distal position, the inner shaft is positioned to directly block the lockout arm to thereby inhibit movement of the trigger to the actuated position and wherein, when the inner shaft is disposed in the proximal position, a clearance is provided to permit movement of the lockout arm, thereby permitting movement of the trigger to the actuated position.

2. The forceps according to claim 1, further comprising a housing having an outer shaft extending distally therefrom, the end effector assembly disposed at a distal end of the outer shaft and the inner shaft slidably disposed within the outer shaft.

3. The forceps according to claim 2, further comprising a drive assembly including a drive bar operably coupled to the end effector assembly, the drive bar sildably disposed within the outer shaft and translatable between a first position and a second position for moving the jaw members between the spaced-apart position and the approximated position.

4. The forceps according to claim 3, further comprising a movable handle coupled to the drive assembly and extending from the housing, the movable handle movable between an initial position and a compressed position for translating the drive bar between the first position and the second position.

5. The forceps according to claim 2, wherein the trigger assembly is disposed within the housing and wherein the trigger extends from the housing.

\* \* \* \* \*